United States Patent [19]

Basalay et al.

[11] Patent Number: 4,519,926
[45] Date of Patent: May 28, 1985

[54] POLYBORATE ESTERS AND THEIR USE IN LUBRICANTS

[75] Inventors: Robert J. Basalay; C. Thomas West; Dennis G. Petrille, all of Naperville, Ill.

[73] Assignee: Standard Oil Company (Indiana), Chicago, Ill.

[21] Appl. No.: 467,951

[22] Filed: Feb. 18, 1983

[51] Int. Cl.$^3$ .................. C10M 1/50; C10M 1/10; C10M 3/02; C10M 7/48
[52] U.S. Cl. .................. 252/49.6; 260/462 R
[58] Field of Search ........... 260/462 R; 252/46.3, 252/49.6

[56] References Cited

U.S. PATENT DOCUMENTS

| | | | |
|---|---|---|---|
| 2,084,261 | 6/1937 | Boughton | 260/462 R |
| 2,642,453 | 6/1953 | Lippincott | 260/462 R |
| 2,721,121 | 10/1955 | Lawrence et al. | 44/76 |
| 2,813,830 | 11/1957 | Trautman | 252/49.6 |
| 2,848,312 | 8/1958 | Liao | 260/462 R |
| 3,099,677 | 7/1963 | Hunter | 260/462 R |
| 3,224,971 | 12/1965 | Knowles et al. | 252/46.3 |
| 3,290,352 | 12/1966 | Marchand et al. | 260/462 R |
| 3,410,913 | 11/1968 | McMahon et al. | 260/426 R X |
| 3,522,286 | 7/1970 | Salvemini et al. | 260/462 R |
| 3,755,408 | 8/1973 | Cuneo | 260/462 R |

OTHER PUBLICATIONS

Steinberg, Organoboron Chemistry, Intersc. Publ., John Wiley & Sons N.Y. pp. 462 to 464 (1964).

*Primary Examiner*—Helen M. S. Sneed
*Attorney, Agent, or Firm*—Richard A. Kretchmer; William T. McClain; William H. Magidson

[57] ABSTRACT

Polyborate ester compositions are prepared by reacting ortho-boric acid with at least one alcohol or phenol in a substantially inert organic liquid, which is immiscible with water and has a boiling point in the range from about 80° to about 300° C. at standard pressure, and by continuously removing the water which is produced by the reaction.

20 Claims, No Drawings

POLYBORATE ESTERS AND THEIR USE IN LUBRICANTS

BACKGROUND OF THE INVENTION

1. Field of the Invention

This invention relates to a method of preparing polyborate esters and the use of these esters in lubricants. More particularly, it relates to a single step process for the preparation of polyborate esters from ortho-boric acid which are useful as wear and oxidation inhibitors in lubricants.

2. Description of the Prior Art

Polyborate esters can be regarded as partially esterified boron oxides. More specifically, these materials contain at least two boron atoms which are attached to each other through an oxygen atom bridge. In addition, they also contain at least one borate ester group of the formula R—O—B< wherein R is either a substituted or unsubstituted hydrocarbyl group. These materials can be linear, branched or cyclic in character. Included within this class are the bis-borate esters such as $(RO)_2$B—O—B$(OR)_2$, $(RO)(HO)B$—O—B$(OR)_2$, $(HO)_2$B—O—B$(OR)_2$, and $(HO)_2B$—O—B$(OH)(OR)$; metaborate esters of the formula:

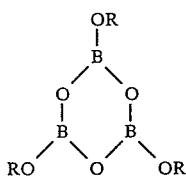

and also a plethora of more complex polymeric materials which, frequently, have a structure which is unknown in detail.

It is known that boric acid can be esterified by reaction with an alcohol as set forth in the following equation:

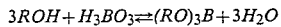

$$3ROH + H_3BO_3 \rightleftharpoons (RO)_3B + 3H_2O$$

It has also been disclosed by U.S. Pat. No. 4,303,445, issued to Whitfield et al. on Dec. 1, 1981, that bis-borate esters can be prepared by the direct reaction of boric acid with an alcohol. However, the borate and polyborate esters are hydrolytically unstable, and water is a product of this type of reaction. As a consequence, this method of preparation is usually not satifactory unless the water can be removed and the reaction forced to completion. The removal of this water is a difficult problem which has not been fully solved.

It is also known that polyborate esters can be prepared by the reaction of boron oxide with esters of ortho-boric acid. However, this method is frequently impractical because of a relatively slow rate of reaction. Examples of this approach are set forth in U.S. Pat. No. 3,099,677, issued to Hunter on July 30, 1963, and U.S. Pat. No. 3,522,286, issued to Salvemini on July 28, 1970.

U.S. Pat. No. 3,755,408, issued to Cuneo on Aug. 28, 1973, discloses a two-step process for the preparation of polyborate esters wherein the first step involves heating a suspension of ortho-boric acid ($H_3BO_3$) at a temperature between 80° and 220° C. in an inert organic liquid to dehydrate the acid, and the second step involves reacting the resulting material with an alcohol or phenol. This patent does not, however, either teach or suggest that these two steps could be combined. Similarly, U.S. Pat. No. 3,202,492, issued to Liao on Aug. 24, 1965, teaches that metaborate esters can be prepared by mixing a monohydroxy alcohol and boron oxide in a 2:1 molar ratio together with an organic solvent, such as benzene, and heating at reflux to azeotropically remove the water of reaction.

U.S. Pat. Nos. 2,721,121 and 2,721,180, both issued to Lawrence et al. on Oct. 18, 1955, disclose that oil-soluble organo-boron compounds can be prepared by passing an oxygen-containing gas through a liquid petroleum fraction having a boiling point in the range from about 350° to about 800° F. (177° to 427° C.) and in the presence of an acid selected from the group consisting of ortho-boric acid and meta-boric acid. It is stated that the products of this process can be described, at least in part, as mono-borate esters and bis-borate esters. It is further disclosed that these products are useful as additives to improve the oxidation or wear characteristics of lubricant compositions.

SUMMARY OF THE INVENTION

The present invention is directed to the discovery that a highly effective wear and oxidation inhibitor for use in lubricants can be prepared by the single step reaction of ortho-boric acid with an alcohol or phenol in a liquid organic diluent.

One embodiment of the invention is a process for the preparation of a polyborate ester composition which comprises reacting ortho-boric acid with at least one hydroxyl-containing compound selected from the group consisting of alcohols of at least 3 carbon atoms and phenols in a substantially inert organic liquid at a temperature in the range from about 80° to about 300° C., wherein said organic liquid is immiscible with water and has a boiling point in the range from about 80° to about 300° C. at standard pressure, the ratio of equivalents of hydroxyl-containing compound to moles of ortho-boric acid is in the range from about 0.5 to about 1.5, and the water which is produced by said reaction is continuously removed.

Another embodiment of the invention is the polyborate ester composition prepared by the process which comprises: (a) reacting ortho-boric acid with at least one hydroxyl-containing compound selected from the group consisting of alcohols of at least 3 carbon atoms and phenols in a substantially inert organic liquid at a temperature in the range from about 80° to about 300° C., wherein said organic liquid is immiscible with water and has a boiling point in the range from about 80° to about 300° C. at standard pressure, the ratio of equivalents of hydroxyl-containing compound to moles of ortho-boric acid is in the range from about 0.5 to about 1.5, and the water which is produced by said reaction is continuously removed; and (b) removing sustantially all of said organic liquid from the product of (a).

A further embodiment of the invention is a lubricant composition which comprises a major portion of lubricating oil in combination with the above-described polyborate ester composition.

An object of this invention is to provide a new process for the preparation of oil-soluble polyborate esters.

Another object of this invention is to provide an improved process for the preparation of oil-soluble polyborate esters.

A further object of this invention is to provide improved polyborate ester compositions for use in lubricating oils to inhibit wear and oxidation.

A further object of this invention is to provide polyborate esters which can be used to improve the tolerance of moisture sensitive lubricant compositions toward water.

A still further object of this invention is to provide an oil-soluble polyborate ester composition which contains reduced haze and sediment.

DETAILED DESCRIPTION OF THE INVENTION

We have found that the oil-soluble polyborate ester compositions which are prepared in accordance with this invention are excellent wear and oxidation inhibitors for use in lubricant compositions. In addition, the polyborate ester compositions of this invention also possess reduced haze and sediment in comparison with products which are prepared by other methods. Further, we have found that the polyborate esters of this invention can be used to improve the tolerance toward water of lubricant compositions which are moisture sensitive.

Although polyborate esters can be prepared by the reaction of boron oxide with alcohols or phenols and by reacting boron oxide with trialkyl borates, we have found that the resulting products usually contain sediments and frequently precipitate a gelatinous material. These oil-insoluble sediments and precipitates render such products unsuitable for incorporation into a lubricant composition unless the product is first filtered. However, we have discovered that the polyborate esters which are prepared according to the method of this invention do not contain sediments and do not throw down precipitates. As a consequence, the polyborate ester compositions of this invention can be directly incorporated into a lubricant composition without filtration.

The polyborate ester compositions of this invention are formed in a single step from ortho-boric acid by reaction with at least one hydroxyl-containing compound selected from the group consisting of alcohols and phenols in a volatile organic liquid which has a boiling point in the range from about 80° to about 300° C. Although a pure alcohol or phenol can be used, it will be appreciated that a mixture of two or more alcohols or phenols can also be employed.

Suitable alcohols or phenols for use in the practice of this invention include all such materials which contain at least 3 carbon atoms. It will be appreciated, of course, that suitable alcohols can contain other functional groups which include, but are not limited to, alkoxy, aryloxy, carboalkoxy and halogen groups. The use of alcohols containing less than 3 carbon atoms is usually undesirable since such alcohols result in the formation of polyborate esters which are oil-insoluble. The process of this invention is preferably carried out with aliphatic alcohols. Monohydroxy alcohols containing from 4 to 18 and preferably from 4 to 8 carbon atoms are particularly suitable since they are readily available and yield polyborate esters having physical properties, such as viscosity and volatility, which render them highly satisfactory for use as lubricant additives. Suitable alcohols include, but are not limited to, 1-hexanol, 1-butanol, 1-pentanol, 2-pentanol, 2-methyl-1-propanol, 4-methyl-2-pentanol, dodecylphenol, nonylphenol, ethylphenol, 2-methyl-2-butanol, 1-octanol, 2-octanol, and 1,6-hexanediol.

The ratio of equivalents of hydroxyl-containing compound to moles of ortho-boric acid in the process of this invention is desirably in the range from about 0.5 to about 1.5 and preferably from about 0.7 to about 1.2. It will be appreciated, of course, that the equivalents of hydroxyl-containing compound are calculated on the basis of the number of hydroxyl groups in this material. For example, when a monohydroxy alcohol or phenol is used, the mole ratio of the alcohol or phenol to ortho-boric acid is desirably in the range from about 0.5 to about 1.5 and preferably from about 0.7 to about 1.2.

The reaction of ortho-boric acid with the hydroxyl-containing compound in accordance with this invention is carried out in a substantially inert organic liquid which is immiscible with water and has a boiling point in the range from about 80° to about 300° C., and preferably from about 100° to about 300° C. This organic liquid is necessary to permit a removal of the water which is formed during the esterification reaction and to ensure the formation of a polyborate ester product which is free of solids. In addition, the organic liquid also permits a convenient control of the reaction mixture viscosity and also promotes contact between the reactants. The organic liquid must be substantially inert with respect to the ortho-boric acid and alcohol or phenol starting materials and the polyborate ester product. Suitable organic liquids include, but are not limited to, benzene, toluene, xylene, ethylbenzene, diethylbenzene, and heptane.

The precise amount of the organic liquid which is used in the practice of this invention is not critical. However, the amount must be adequate to permit a removal of the water which is formed during the esterification reaction. In addition, the amount of the organic liquid is preferably in excess of the amount which is required for the formation of a dispersion with the ortho-boric acid.

The reaction of ortho-boric acid with the hydroxyl-containing compound in accordance with this invention can be carried out at a temperature in the range from about 80° to about 300° C., and preferably from about 80° to about 200° C. The reaction is conveniently carried out at reflux temperature in an organic liquid having a boiling point within this temperature range. If desired, the reaction can be carried out under an inert atmosphere, such as nitrogen, to preclude any possible decomposition as a consequence of air oxidation.

The water which is formed during the course of the reaction must be removed as it is formed. This is facilitated by the organic liquid and can be conveniently accomplished by conducting the reaction at reflux temperature in an organic liquid which forms a lower boiling azeotrope with water and removing the water by distillation of the azeotrope from the reaction mixture. Such organic liquids include, for example, benzene, toluene and xylene.

The ortho-boric acid can be incorporated into the reaction mixture as a pure solid. However, a highly desirable alternative involves adding the ortho-boric acid as a slurry or suspension in a mineral oil. This alternative improves the ease with which the ortho-boric acid can be handled during the practice of the subject process since the slurry or suspension can be manipulated as a liquid rather than a solid.

Upon completion of the reaction between the ortho-boric acid and the hydroxyl-containing compound, the polyborate ester product can be isolated by removal of the organic liquid. The organic liquid can be removed by conventional techniques, for example, by distillation. If desired, a stream of inert gas, such as nitrogen, can be passed through the heated material to either facilitate or complete the removal of the organic liquid.

A preferred embodiment of the process of this invention involves reacting the ortho-boric acid with the hydroxyl-containing compound in a mixture of the volatile organic liquid with a lubricating oil. Suitable lubricating oils for this purpose are immiscible with water and have a boiling point in excess of about 300° C. at standard pressure. Such lubricating oils include, but are not limited to, mineral oils and olefin polymers. However, mineral oils are generally preferred. The amount of lubricating oil which is incorporated into the reaction mixture in this embodiment of the invention can vary widely, for example, from about 0.3 to about 20 times and perferably from about 0.5 to about 2 times the combined weight of ortho-boric acid and hydroxyl-containing compound.

The additional presence of a lubricating oil in the reaction mixture of this invention is highly desirable for two principal reasons. First of all, the oil is relatively nonvolatile and remains with the polyborate ester product when the more volatile organic liquid is removed from the reaction mixture. The result is a polyborate ester concentrate in a lubricating oil which is highly satisfactory for use as a blending component in the preparation of finished lubricant compositions. The pure polyborate esters which are prepared by the process of this invention are frequently quite viscous, and the lubricating oil of the concentrate serves to improve their handling properties. Secondly, polyborate esters are hydrolytically unstable and decompose rapidly upon contact with water. The lubricating oil in this directly produced concentrate is immiscible with water and, therefore, serves to protect the polyborate ester from contact with atmospheric moisture and accidental contact with water.

The polyborate esters prepared in accordance with the process of this invention can be incorporated into a lubricating oil by simple mixing. Suitable lubricating oils include, for example, mineral oils; synthetic materials such as olefin polymers, polyoxypropylene and certain dicarboxylic acid diesters; vegetable oils such as cottonseed oil, corn oil and castor oil; and animal oils such as lard oil and sperm oil. A lubricating oil composition will typically comprise a major portion of a lubricating oil in combination with the polyborate ester product, wherein the amount of polyborate ester product is from about 0.01 to about 15 weight percent of the lubricating oil composition.

Concentrates containing from about 5 to about 75 weight percent or more of the subject polyborate ester product in a suitable base oil, either alone or in combination with other well known lubricant additives, can be used for blending with lubricating oils in the proportions desired for particular conditions or used to give a finished product containing from about 0.01 to about 15 weight percent of the polyborate ester product.

The polyborate ester product of this invention can be used in combination with other conventional lubricating oil additives which include, but are not limited to, wear inhibitors, extreme pressure agents, friction modifiers, antioxidants, corrosion inhibitors, detergents, dispersants, antifoam agents, viscosity index improvers, and pour point depressants.

The following examples are intended only to illustrate the invention and are not to be construed as imposing limitations on it.

EXAMPLE I

A mixture of 814 grams (11.0 moles) of 2-methyl-1-propanol and 620 grams (10.0 moles) of orthoboric acid in 400 grams of toluene was heated at reflux temperature under atmospheric pressure with continuous removal of water by azeotrope formation. After 8 hours, 375 milliliters of water (102% of theory) had been collected. Toluene was distilled from the resulting clear reaction mixture, with the residue being heated to a final temperature of 166° C. Residual traces of toluene were then removed by passing a stream of nitrogen through the residue at a temperature of 166° C. for 1 hour. The resulting polyborate ester was a clear liquid which contained 8.4% boron.

EXAMPLE II

A mixture of 550 grams (5.38 moles) of 1-hexanol and 310 grams (5.01 moles) of ortho-boric acid in 300 grams of xylene was heated at reflux temperature under atmospheric pressure with continuous removal of water by azeotrope formation. After the collection of 179 milliliters of water (97% of theory), xylene was removed from the reaction mixture by passing a stream of nitrogen through it at a rate of 0.94 liter/minute over a period of one hour at a temperature of 182° C. The resulting polyborate ester was a clear liquid which contained 7.7% boron.

EXAMPLE III

A mixture of 550 grams (5.38 moles) of 4-methyl-2-pentanol and 310 grams (5.01 moles) of orthoboric acid in 300 grams of xylene was heated at reflux temperature under atmospheric pressure with continuous removal of water by azeotrope formation. When water evolution from the reaction mixture stopped, volatile material was removed by passing a stream of nitrogen through the mixture at a rate of 0.71 liter/minute over a period of one hour at a temperature of 182° C. The resulting polyborate ester was a clear liquid which contained 6.4% boron.

EXAMPLE IV

A mixture of 407 grams (5.49 moles) of 1-butanol and 310 grams (5.01 moles) of ortho-boric acid in 200 grams of xylene was heated at reflux temperature under atmospheric pressure with continuous removal of water by azeotrope formation. After the collection of 184 milliliters of water (100% of theory), volatile material was removed from the mixture by passing a stream of nitrogen through it over a period of one hour at 182° C. The resulting polyborate ester was a clear liquid which contained 9.4% boron.

EXAMPLE V

A mixture of 500 grams (6.75 moles) of 1-butanol and 70 grams (1.01 moles) of boron oxide in 100 grams of toluene was heated at reflux temperature under atmospheric pressure with continuous removal of water by azeotrope formation. After the collection of 57 milliliters of water, an additional 120 grams (1.72 moles) of boron oxide were added and the heating with removal of water was continued until an additional 22 milliliters of water had been collected. Toluene was distilled from the resulting mixture, with the residue being heated to a final temperature of 171° C., to give a clear liquid product which contained 7.2% boron. However, a precipitate separated from the product after standing at room temperature overnight.

EXAMPLE VI

The ability of the polyborate ester product of Example II to serve as a wear inhibitor when incorporated into a lubricating oil composition was evaluated in a Ford 2.3 liter engine using the two lubricating oil formulations which are set forth in Table I. Using a new camshaft for each test run, cam wear in the engine was evaluated after 96 hours of operation with each formulation. Lubricant A, which contained no polyborate ester, resulted in an average cam wear of 41 microns. Lubricant B, which contained 0.52 weight percent of the polyborate ester of Example II, resulted in an average cam wear of 24 microns. Consequently, use of the polyborate ester resulted in a 41 percent reduction in average cam wear.

TABLE I

| Component[1] | Lubricant A[2] | Lubricant B[2] |
|---|---|---|
| Base Oil | 76.6 | 76.1 |
| Mannich Dispersant | 5.5 | 5.5 |
| Overbased Calcium Phenate | 3.6 | 3.6 |
| Zinc Dihydrocarbyl Dithiophosphate | 1.49 | 1.49 |
| Overbased Magnesium Sulfonate | 0.5 | 0.5 |
| Calcium Sulfonate | 2.5 | 2.5 |
| Rust Inhibitor | 0.2 | 0.2 |
| Olefin Copolymer Viscosity Index Improver | 9.6 | 9.6 |
| Polyborate Ester of Example I | 0.0 | 0.52 |

[1]The various additives and their amounts used in the preparation of lubricants A and B were identical except that lubricant A contained no polyborate ester.
[2]The amount of each component is expressed in weight percent.

We claim:

1. A process for the preparation of a polyborate ester composition which comprises reacting ortho-boric acid with at least one hydroxyl-containing compound selected from the group consisting of monohydroxy alcohols of at least 3 carbon atoms and monohydroxy phenols in a mixture of a volatile organic liquid and a lubricating oil at a temperature in the range from about 80° to about 300° C., wherein said volatile organic liquid is substantially inert and immiscible with water and has a boiling point in the range from about 80° to about 300° C., at standard pressure, said lubricating oil is immiscible with water and has a boiling point in excess of about 300° C. at standard pressure, the amount of said lubrication oil is from about 0.3 to about 20 times the combined weight of said ortho-boric acid and hydroxyl-containing compound, the ratio of equivalents of hydroxyl-containing compound to moles of ortho-boric acid is in the range from about 0.5 to about 1.5, and the water which is produced by said reaction is continuously removed by azeotrope formation with said volatile organic liquid.

2. The process as set forth in claim 1 wherein said hydroxyl-containing compound is selected from the group consisting of monohydroxy aliphatic alcohols.

3. The process as set forth in claim 2 wherein said hydroxyl-containing compound is selected from the group consisting of monohydroxy aliphatic alcohols which contain from 4 to 8 carbon atoms.

4. The process as set forth in claim 3 wherein the ratio of equivalents of hydroxyl-containing compound to moles of ortho-boric acid is in the range from about 0.7 to about 1.2.

5. The process as set forth in claim 4 wherein said volatile organic liquid is selected from the group consisting of benzene, toluene and xylene.

6. The process as set forth in claim 5 wherein said lubricating oil is a mineral oil.

7. The process as set forth in claim 6 wherein the amount of said mineral oil is from about 0.5 to about 2 times the combined weight of said ortho-boric acid and hydroxyl-containing compound.

8. The polyborate ester composition prepared by the process which comprises:
  (a) reacting ortho-boric acid with at least one hydroxyl-containing compound selected from the group consisting of monohydroxy alcohols of at least 3 carbon atoms and monohydroxy phenols in a mixture of a volatile organic liquid and a lubricating oil at a temperature in the range from about 80° to about 300° C., wherein said volatile organic liquid is substantially inert and immiscible with water and has a boiling point in the range from about 80° to about 300° C. at standard pressure, said lubricating oil is immiscible with water and has a boiling point in excess of about 300° C. at standard pressure, the amount of said lubricating oil is from about 0.3 to about 20 times the combined weight of said ortho-boric acid and hydroxyl-containing compound, the ratio of equivalents of hydroxyl-containing compound to moles of ortho-boric acid is in the range from about 0.5 to about 1.5, and the water which is produced by said reaction is continuously removed by azeotrope formation with said volatile liquid; and
  (b) removing substantially all of said volatile organic liquid from the product of (a).

9. The composition as set forth in claim 8 wherein said hydroxyl-containing compound is selected from the group consisting of monohydroxy aliphatic alcohols.

10. The composition as set forth in claim 9 wherein said hydroxyl-containing compound is selected from the group consisting of monohydroxy aliphatic alcohols which contain from 4 to 8 carbon atoms.

11. The composition as set forth in claim 10 wherein the ratio of equivalents of hydroxyl-containing compound of moles of ortho-boric acid is in the range from about 0.7 to about 1.2.

12. The composition as set forth in claim 11 wherein said volatile organic liquid is selected from the group consisting of benzene, toluene and xylene.

13. The composition as set forth in claim 12 wherein said lubricating oil is a mineral oil.

14. The composition as set forth in claim 13 wherein the amount of mineral oil is from about 0.5 to about 2 times the combined weight of said ortho-boric acid and hydroxyl-containing compound.

15. The composition as set forth in claim 12 wherein said reaction is carried out at a temperature in the range from about 80° to about 200° C.

16. A lubricant composition comprising a major portion of a lubricating oil in combination with a polyborate ester composition wherein the amount of said polyborate ester composition is from about 0.01 to about 15 weight percent of said lubricant composition and wherein said polyborate ester composition is prepared by the process which comprises:
  (a) reacting ortho-boric acid with at least one hydroxyl-containing compound selected from the group consisting of monohydroxy alcohols of at least 3 carbon atoms and monohydroxy phenols in a substantially inert organic liquid at a temperature in the range from about 80° to about 300° C., wherein said organic liquid is immiscible with water and has a boiling point in the range from about 80° to about 300° C. at standard pressure, the ratio of equivalents of hydroxyl-containing compound to moles of ortho-boric acid is in the range from about 0.5 to about 1.5, and the water which is produced by said reaction is continuously removed; and (b) removing substantially all of said organic liquid from the product of (a).

17. The composition as set forth in claim 16 wherein said water is removed by azeotrope formation with said organic liquid.

18. The composition as set forth in claim 17 wherein said hydroxyl-containing compound is selected from the group consisting of monohydroxy aliphatic alcohols which contain from 4 to 8 carbon atoms.

19. The composition as set forth in claim 18 wherein the ratio of equivalents of hydroxyl-containing compound to moles of ortho-boric acid is in the range from about 0.7 to about 1.2.

20. The composition as set forth in claim 19 wherein said organic liquid is selected from the group consisting of benzene, toluene and xylene.

* * * * *

UNITED STATES PATENT OFFICE
CERTIFICATE OF CORRECTION

Patent No. 4,519,926                    Dated May 28, 1985

Inventor(s) Robert J. Basalay, C. Thomas West and Dennis G. Petrille

It is certified that error appears in the above-identified patent and that said Letters Patent are hereby corrected as shown below:

Column 6, line 7, "orthoboric" should read --ortho-boric--.

Column 6, line 35, "orthoboric" should read --ortho-boric--.

Column 7, line 48, "C., at standard" should read --C at standard--.

Column 7, lines 50 & 51, "lubrication oil" should read --lubricating oil--.

Column 8, line 45, "of moles of" should read --to moles of--.

Signed and Sealed this

Fifteenth Day of October 1985

[SEAL]

Attest:

Attesting Officer

DONALD J. QUIGG

Commissioner of Patents and Trademarks—Designate